United States Patent
Corby, Jr.

[11] Patent Number: 5,774,212
[45] Date of Patent: Jun. 30, 1998

[54] METHOD AND APPARATUS FOR DETECTING AND ANALYZING DIRECTIONALLY REFLECTIVE SURFACE FLAWS

[75] Inventor: Nelson Raymond Corby, Jr., Scotia, N.Y.

[73] Assignee: General Electric Co., Schenectady, N.Y.

[21] Appl. No.: 821,676

[22] Filed: Mar. 19, 1997

[51] Int. Cl.$^6$ ................................................. G01N 21/00
[52] U.S. Cl. .......................................... 356/237; 356/445
[58] Field of Search .................................... 356/375, 376, 356/394, 237, 402–411, 30, 286, 445–448; 348/86, 91, 92, 94, 95, 96, 125, 129, 130, 131

[56] References Cited

U.S. PATENT DOCUMENTS

| | | | |
|---|---|---|---|
| 3,782,836 | 1/1974 | Fey et al. | 356/30 |
| 5,229,841 | 7/1993 | Taranowski et al. | 356/407 X |
| 5,245,671 | 9/1993 | Kobayashi et al. | 356/237 |
| 5,477,371 | 12/1995 | Shafir | 356/376 X |

*Primary Examiner*—K. Hantis
*Attorney, Agent, or Firm*—Nixon & Vanderhye

[57] ABSTRACT

An inspection system for imaging and analyzing anisotropically reflecting surface flaws uses a side-looking borescope-type optical probe device for acquiring images of a region on the surface of an object and a computer for analyzing the images. The head of the probe includes a special integral lighting arrangement for illuminating the surface of the object in a manner that assures detection of anisotropically reflecting surface flaws. The borescope configuration of the optical probe along with its integral lighting and imaging arrangement allows it to be used in spatially confined environments where conventional methods and equipment for viewing anisotropically reflecting surface flaws would not be feasible. The special lighting arrangement employs multiple single light sources arranged in a circular array around a central image receiving device. Light sources in the array are individually and sequentially activated in a progressive manner such that light emanating from the array changes position in an orbital fashion about the image receiving device. Video images of the surface are acquired for each distinct direction of illumination. The acquired images are simultaneously displayed in real time on a monitor and are also stored for further analysis and processing. Features of an imaged area which are likely to be significant are displayed enhanced or otherwise marked on the same or a secondary monitor so as to alert an operator to suspect regions.

13 Claims, 4 Drawing Sheets

METHOD AND APPARATUS FOR DETECTING AND ANALYZING DIRECTIONALLY REFLECTIVE SURFACE FLAWS

TECHNICAL FIELD

The present invention relates to a method and apparatus for detection of surface flaws on an object and more specifically, to a method and apparatus for detecting surface flaws in directionally solidified metallic castings, parts and machine elements.

BACKGROUND

In inspecting many materials for flaws, it is often necessary to be able to recognize characteristic indications on the surface of the object being inspected. Typical surface flaws may be discolorations, cracks, pits, rough spots, etc. Some surface flaws can be said to be "isotropic"—that is, they appear the same over a large range of viewing angles and incident lighting directions—while other flaws can be said to be "anisotropic"—that is, the appearance and detectability of a surface flaw depends heavily on the relative orientations of the object's surface, the viewer's perspective (position) and the direction of incident lighting used to illuminate the object surface.

Surface flaws in directionally solidified metallic castings typically appear in small linear patterns that have a reflectivity that is different from the parent material surrounding the flaw. This phenomenon is thought to arise from the slightly differing angular orientation of metallic crystals in the flaw compared to the angular orientation of crystals in the surrounding area. Such flaws are commonly termed "splinters". Another example of such anisotropically reflecting features of an object is the small scratches on the surface of a polished metal object or oily films on the surface of glass. Conventionally, to elicit this optical phenomenon, a human inspector must physically arrange a lighting source and then hold and orient the inspected object in just such a way so as to reflect light from the flaw than the surrounding area, causing the flaw to appear darker or lighter than the surrounding area. Unfortunately, in many environments, and, in particular, during the course of an automated inspection procedure, it may be impractical or impossible to independently adjust the relative positions and orientation of an object to be inspected, an illuminating light source and the human observer—or, as the case may be, an imaging device for recording or providing remote inspection capabilities. Take, for example, an inspection arrangement having an object resting in a fixed position with respect to a scanning gantry mounted TV camera. In this case, there can be no assurance that surface flaw orientations will be favorably aligned with the scanning gantry camera and the particular light sources available. Moreover, the difference in contrast between the flaw and the surrounding surface may not always be sufficient to enable casual detection by the naked eye even if the relative orientation of an object, an observer, and the illuminating light is proper and optimal.

There are also numerous situations and environments where an inspection of the surface of an object is desired but, due to space limitations, it is impossible to correctly position an inspector or even a small imaging device at the proper viewing location and orientation. Accordingly, a need exists for a surface inspection apparatus having some sort of source lighting arrangement that does not require positional adjustments, but nonetheless has the ability to detect anisotropically reflecting flaws regardless of the orientation of the flaw with respect to the inspector or imaging device. Moreover, it would be desirable to have a surface inspection device that could enhance one's ability to distinguish flaws of low optical contrast with respect to the surrounding area or at least draw one's attention to suspect areas where such flaws are likely to exist. In addition, visual inspection systems that rely solely on a human inspector's ability to detect flaws are subject to an increased potential for error or omissions. In particular, where large surface areas must be meticulously inspected, the process can be especially fatiguing, or even boring to the extent that a human inspector is likely to miss or not recognize a flaw or a potential problem area.

DISCLOSURE OF THE INVENTION

The present invention addresses the above problems by providing a method and apparatus for imaging directionally reflective surface flaws of objects located in spatially compromised environments while also providing improved detection capabilities. In accordance with the present invention, a visual image acquiring device (such as a TV camera or other appropriate optics) is integrated in a compact probe apparatus having an optical mechanism for illuminating the surface of an object under inspection. The probe is compact enough to be used in environments having very limited clearance between objects inspected and the integrated arrangement of imaging and illumination mechanisms allows for detection and observation of anisotropic surface flaws regardless of the orientation of the flaw with respect to the probe.

In addition, the present invention contemplates providing an anisotropic surface flaw inspection system that incorporates a video frame store memory and a computer for processing sequential video frame images for real time display enhancement of potential flaw features. This process is accomplished in such a manner so as to effectively increase the sensitivity of a human observer to the presence of a surface flaw.

Figure 1:
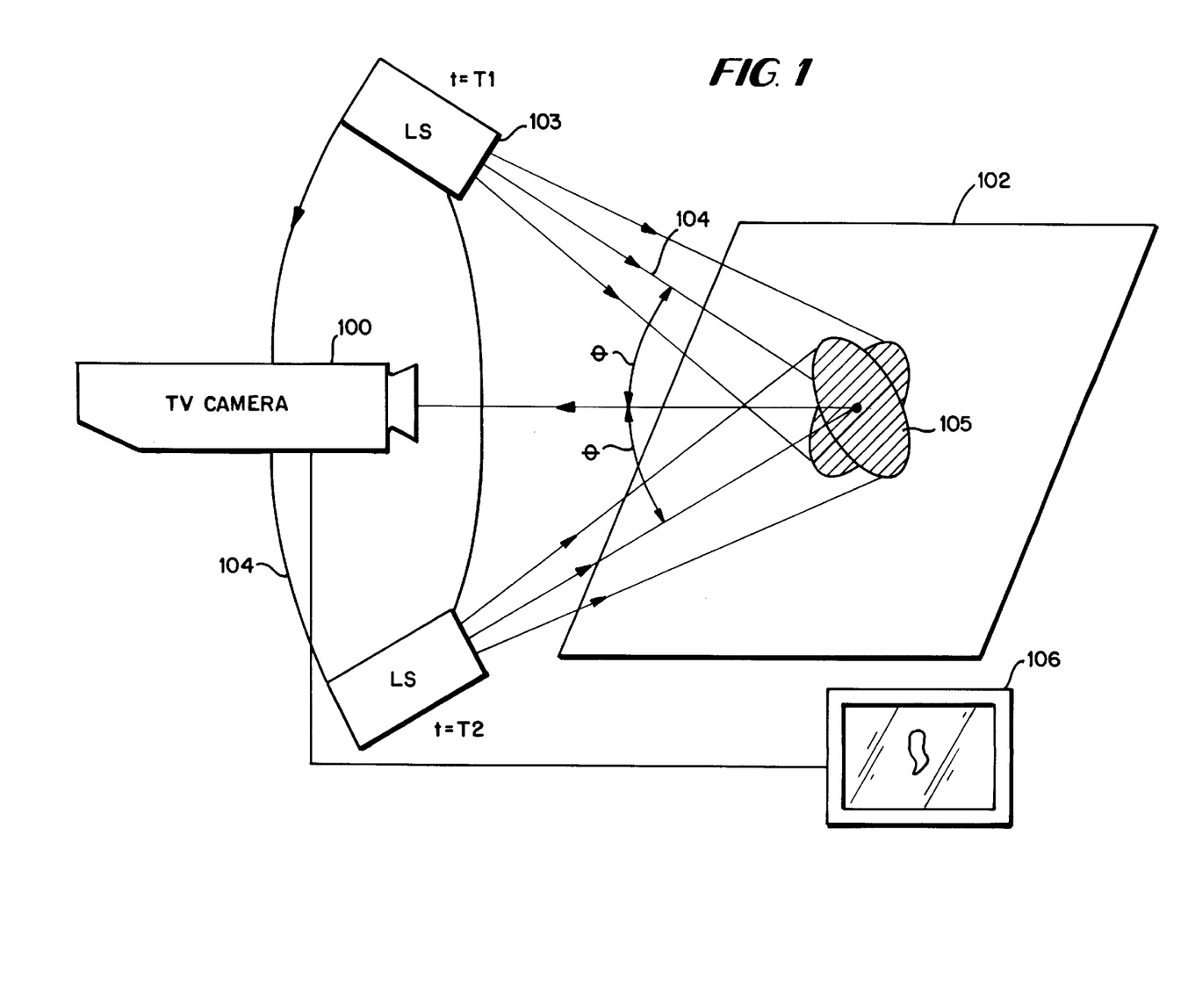
FIG. 1 is a diagrammatic illustration of a surface imaging and surface illumination arrangement for the detection of directionally reflective (anisotropic) surface flaws in accordance with the basic concepts of the present invention.

The basic arrangement for a surface flaw inspection apparatus in accordance with the present invention is depicted in FIG. 1. Essentially, the present invention consists of a camera (or other imaging device) directed toward and focused on a section of the surface of an object under inspection while illuminating the surface by a special light source whose position and/or possibly angular orientation, is varied in a periodic repeatable manner. As depicted in FIG. 1, a light source (LS) 103 is caused to "orbit" the longitudinal axis of a video camera 100. For the sake of simplicity, FIG. 1 illustrates light source 103 only at times $T_1$ and $T_2$ of the many possible positions during its orbit. As light source 103 is made to orbit camera 100, its central axis of illumination 104 with respect to illuminated area 105 is maintained substantially at a fixed angle θ, with respect to the central axis of camera 100.

This method of lighting the surface ensures that any directionally reflective surface flaws within area 105 will be illuminated from a full circle of source directions relative to the camera axis. This is important because, for at least some limited number of possible light source orientations, the appearance of an anisotropically reflecting surface flaw will be significantly different from that of the surrounding unflawed surface area depending on the direction of incident illumination. However, since an optimal direction for the incident insure illumination cannot be known a priori, surface region 105 is progressively illuminated throughout an entire 360° rotation cycle of the orbiting light source. As light source 103 orbits around camera 100, an image of illuminated area 105 is captured by the camera and displayed on video monitor 106. Preferably, the image is recorded over the course of numerous orbits. Alternatively, the eye of the observer or other appropriate optical elements for enhancing or recording a visual image may be substituted for camera 100.

Since the human eye is known to be sensitive to pulsating, time varying patterns, the present invention takes advantage of this phenomenon to further enhance visual detection of flaws. Specifically, light source 103 is preferably made to orbit camera 100 repetitively at a relatively rapid rate. This repetitive illumination from different source directions will cause an anisotropic surface flaw to "flash" or pulsate (once or more per orbit), hence, drawing attention to and significantly enhancing perception of any potential problem areas.

In accordance with a further aspect of the present invention, sequential video frame images of the illuminated area on an object surface are captured and stored in a video frame store memory over the course of one or more orbits of the illuminating orbiting light source. Each stored image corresponds to the surface illuminated from a particular direction. A gray scale histogram of intensities of image pixels is complied for each stored video frame information by an image processing computer and used to identify potential or unobvious flaws which would otherwise be difficult or impossible to detect. Additionally, the system image processing computer is used to perform other analytical tasks such as calculating various physical characteristics of detected flaws (such as area, location, length, width, etc.) from the video image and cataloging the characteristics data for future analysis.

BRIEF DESCRIPTION OF THE DRAWINGS

These and other features and advantages of the present invention will become more completely understood by referring to the following detailed description of presently preferred exemplary embodiments in conjunction with the FIGURES in which like reference numerals refer to like elements throughout.

BEST MODE FOR CARRYING OUT THE INVENTION

In the following description, for purposes of explanation and not limitation, specific details are set forth, such as particular circuits, circuit components, interfaces, techniques, etc. in order to provide a thorough understanding of the present invention. However, it will be apparent to one skilled in the art that the present invention may be practiced in other embodiments that depart from these specific details. In other instances, detailed descriptions of well known methods and programming procedures, devices, and circuits are omitted so not to obscure the description of the present invention with unnecessary detail.

As discussed above, FIG. 1 shows a conceptual arrangement of the basic method and apparatus of the present invention. Camera 100 is focused at an area 105 on a surface 102 of an object under inspection. Light source 103 is made to orbit camera 100 at a fixed angle of orientation and distance with respect to surface 102 so as to provide illumination over a small area 105 covering the focal point of camera 100. In this figure, light source 103 is shown positioned at two points in its orbit about camera 100, at times $T_1$ and $T_2$. As light source 103 orbits camera 100, the direction of incident light—as distinguished from the angle, $\theta$, of incident light with respect to surface 102—is constantly changing. (The incident angle $\theta$ is shown here as a constant for the sake of simplicity. Although it is not necessarily changed in this particular example, the present invention contemplates other embodiments in which the angle $\theta$ is also varied). This constantly changing direction of incident light will at some point cause an anisotropic surface flaw to appear different in contrast with respect to the background or surrounding surface region. While light source 103 is orbiting camera 100, an image of illuminated area 105 is displayed on video monitor 106 for viewing in "real time" by a human operator.

Detectable differences in contrast between the flaw and surrounding area are usually visible for only a limited number of incident light directions. Consequently, as light source 103 progresses in its orbit around camera 100, a surface flaw will appear to fade in and out of view. If the light source 103 is made to orbit rapidly about camera 100, anisotropically reflecting flaws will appear to "flash" or pulsate at a rate comparable to the orbital frequency of the orbiting light source 103. Preferably, the orbital rate of light source 103 is chosen such that the image of a flaw and the appearance of the background will vary differentially at a rate which is optimally perceptible to a human observer. In addition, the particular wavelength of the orbiting light source used to illuminate the surface may be altered to maximize the difference in contrast between the flaw and surrounding area.

Figure 2:
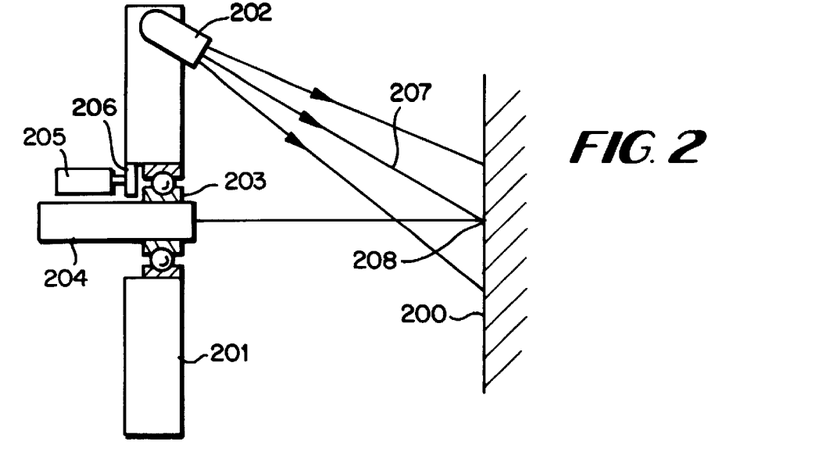
FIG. 2 is a cross-sectional side view of an example embodiment of a mechanically driven anisotropic surface flaw inspection apparatus using a single orbiting light source in accordance with the present invention.

FIG. 2 shows one possible example embodiment of the invention that utilizes a motor driven rotating disk arrangement to provide the desired illumination. In this embodiment, a cut-away side view of the imaging and illuminating mechanism and the illuminated surface 200 of an object under inspection is depicted. An annular disk, 201, supporting a small incandescent spot lamp, 202, is mounted on a doughnut-shaped roller bearing 203 that has a video camera 204 in its central aperture. A motor 205 employs a drive wheel 206 to rotate disk 201 causing lamp 202 to orbit camera 204 at a constant rate. Lamp 202 is provided with electrical power via an internal battery or, alternatively, an appropriate slip-ring power connection arrangement (not shown) may be provided. Preferably, a central axis 207 of a cone of illumination from lamp 202 is aligned so that it intersects camera axis 208 approximately at the plane of focus on object surface 200. Other suitable drive arrangements may also be employed for rotating disk 201 to cause lamp 202 to orbit camera 204.

Figure 3A:
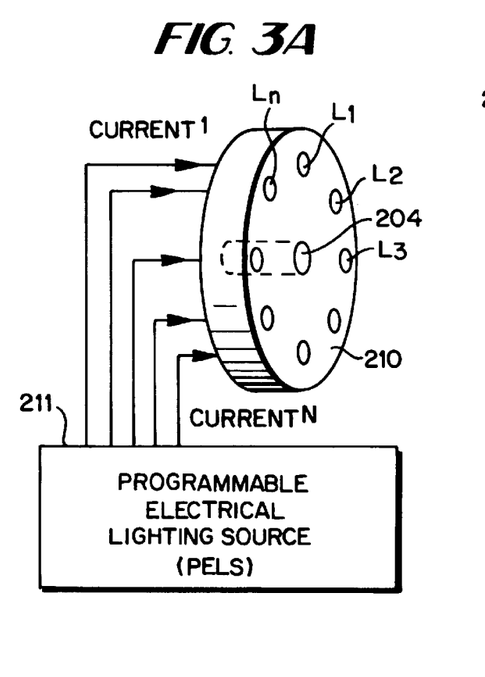
FIG. 3A is a diagrammatic illustration of an electrically programmable surface illumination mechanism using multiple light emitting sources in accordance with the present invention.
Figure 3B:
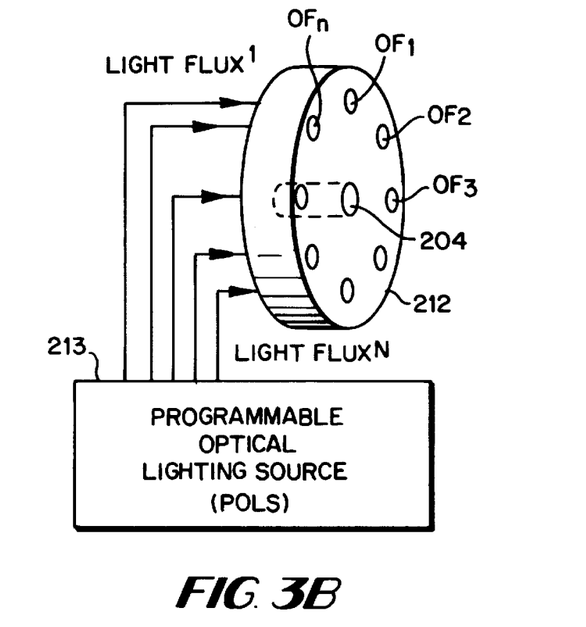
FIG. 3B is a diagrammatic illustration of an electrically programmable surface illumination mechanism using multiple optical fibers in accordance with the present invention.
Figure 3C:
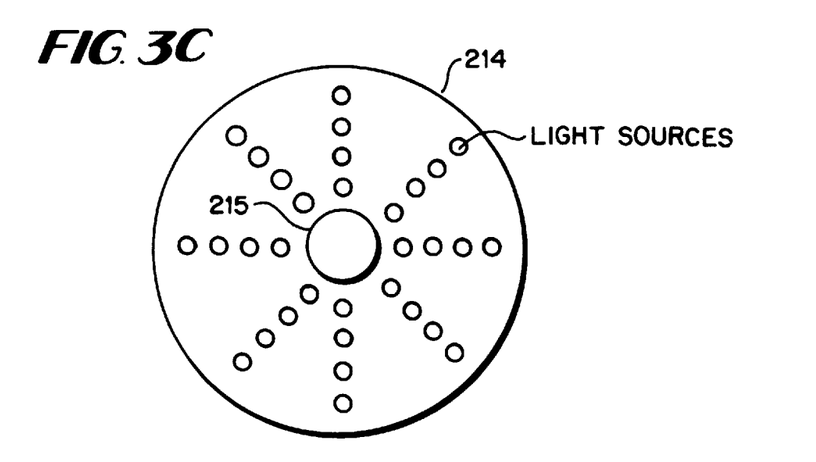
FIG. 3C is a diagrammatic illustration of one possible example configuration for an arrangement of light sources on the surface illumination mechanism of the present invention.

FIGS. 3A–3C show alternate embodiments of the invention that utilize an array of stationary light sources to achieve substantially the same effect as the single rotating illumination source 202 of FIG. 2. In a first embodiment shown in FIG. 3A, camera 204 is centrally mounted in support structure 210 and the physically rotating light source of FIG. 2 is replaced by a circular array (or ring) of fixed illumination sources, $L_1$–$L_n$, such as small lamps or light emitting diodes. In this embodiment, light source support structure 210 remains fixed with respect to camera 204. In order to create the effect of an orbiting light source, a conventional programmable electrical lighting source (PELS) 211 is used to periodically and sequentially cause activation of lights $L_1$ through $L_N$. If lights $L_1$ through $L_N$ are progressively turned on and off for sequential non-overlapping periods, the practical effect is somewhat similar to the physically orbiting light source of FIG. 2. In addition, "programmable" electrical lighting current source 211 allows the number, pattern and frequency of lamp activation to be controlled in such a manner that it can easily simulate either single or multiple light sources orbiting at various speeds.

FIG. 3B shows an alternative embodiment that utilizes a plurality of light conducting optical fibers that terminate in a ring—shaped array arranged around central video camera 204. The optical fibers are coupled to a programmable optical light supply (POLS) 213 which provides light in a controlled sequence to one end of each fiber. Distal ends of fibers $OF_1$–$OF_n$ are fitted into accommodating holes in a support structure 212 surrounding central video camera 204 (or other appropriate imaging optics). Thus, POLS 213 provides light to each optical fiber in a controllable sequential fashion to create the effect of an orbiting light source in the same manner as the embodiment of FIG. 3A.

Figure 4A:
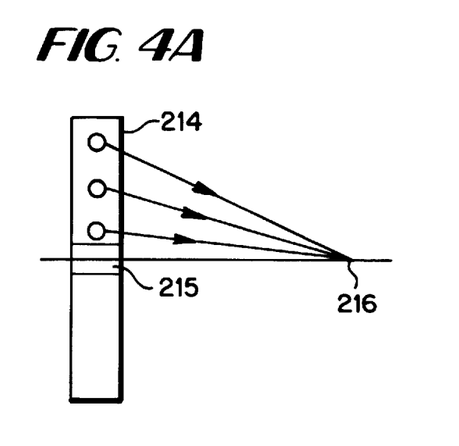
FIGS. 4A and 4B illustrate respectively two example arrangements for the angular orientation of the central illumination axis of light sources in an array on the surface illumination mechanism of the present invention.
Figure 4B:
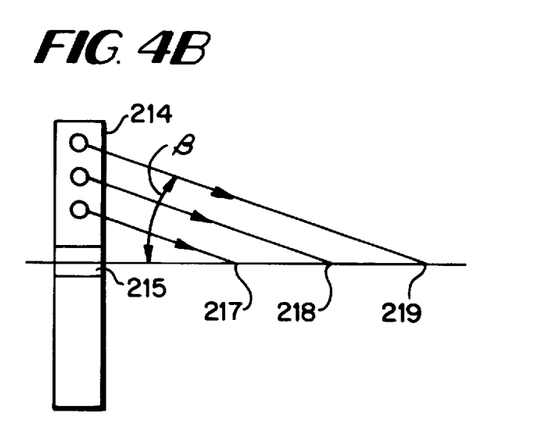

FIG. 3C shows an example of alternative arrangements for the configuration of light sources on the light support structures of the embodiments of FIGS. 3A and 3B. In this example, an array of multiple light sources mounted on support structure 214 are arranged in a series of concentric rings around a central imaging aperture 215. FIGS. 4A and 4B illustrate two possible configurations for orienting the center axes of illumination of the lights in the array of FIG. 3C. For example, in FIG. 4A, the axis of illumination of each light source all coincide at an identical point 216 along the axis of the centrally located imaging device or aperture 215. This arrangement may be used to provide illumination at various angles of incidence with respect to an object's surface and the central axis. FIG. 4B shows a different arrangement wherein an incident angle β with respect to the central axis is the same for all of the illumination sources. In this example, the point where the axes of illumination for each light source intersect with the central axis of imaging aperture 215 occurs at different distances (217, 218 and 219) from light source support structure 214. Such an arrangement is useful, for example, in accommodating objects requiring a large focal depth of field.

Figure 5:
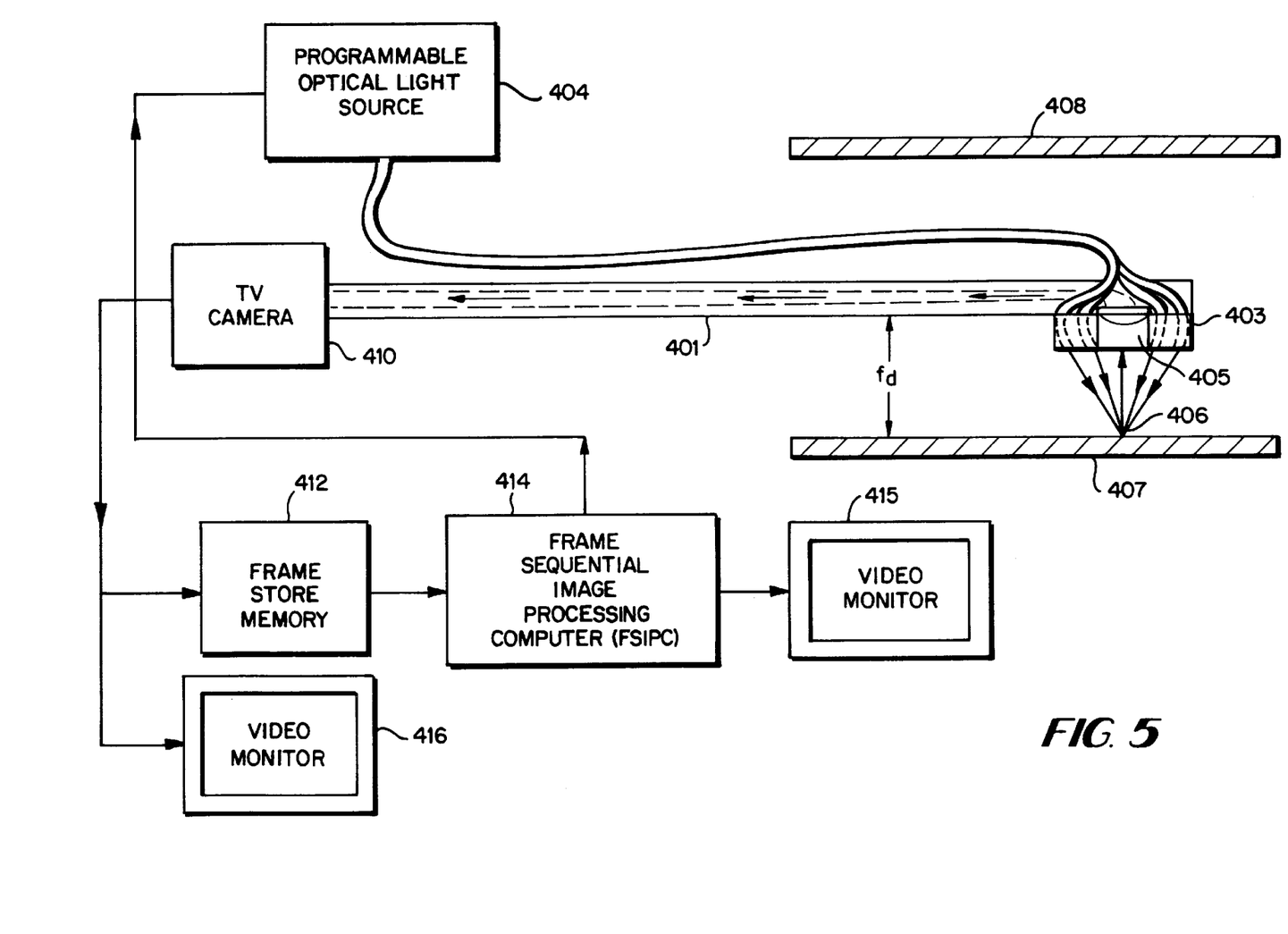
FIG. 5 is a block diagram of the surface flaw inspection system of the present invention incorporating a side view illustration of the preferred embodiment of a baroscope-type probe apparatus in accordance with the present invention.

Referring now to FIG. 5, a preferred embodiment of a surface inspection system for detecting and imaging anisotropically reflecting surface flaws in accordance with the present invention is discussed. The inspection system shown utilizes a "side-looking" type borescope probe arrangement 401 that basically consists of a long narrow tube member having a video camera at a proximal end, an imaging aperture on one side at the distal end, and some integral optical device or apparatus to relay the field of view from the imaging aperture to the remote video camera. In a presently preferred embodiment, the imaging aperture at the distal end of the borescope is provided with a fiber optic surface illumination arrangement as shown in FIG. 3B. Fiber optical cable is also the preferable method used to convey the field of view from the imaging aperture to the remote video camera, however, any other appropriate optical apparatus or arrangement may also be used to carry the image. For example, an alternative arrangement may employ the use of an ultra-miniature video camera, or a light sensitive semiconductor chip, mounted in the imaging aperture at the distal end of the borescope and connected via electric cable to a remote monitor. The borescope structure of probe 401 is provided to allow the use of the probe in spatially confined (limited) environments, as illustrated in FIG. 5 by the position of the probe between opposing object surfaces 407 and 408 or within a cylinder. Preferably, probe 401 is moved in a scanning fashion over surface 407 at a relatively constant "optimal" focusing distance, $f_d$, from the surface.

In the presently preferred embodiment, surface illumination mechanism structure 403 consists of an annular-shaped support member, 403, having a central imaging aperture 405 surrounded by a circular array of light sources as discussed above in the description of FIG. 3B. Each light source consists of a separate light conducting optical fiber, originating from programmable optical light source 404 and terminates in member 403. Each optical fiber is fitted to corresponding holes in support member 403 that are oriented so as to direct light at a common point 406 on surface 407. As light emanates from each of the different light sources in the circular array of member 403, it impinges on the object surface from a slightly different direction. Reflected light is then captured by conventional optics located at central imaging aperture 405 and conveyed via optical fiber to remote camera 410. Assuming that the illuminating light emanating from the end of an optical fiber will cover a cone of approximately 50°–70°, the central axis of each optical fiber (and hence the resulting cone of emanating illumination) should be oriented so as to intersect substantially at a common point 406 on the surface of object 407.

In accordance with the present invention, POLS 404 remotely applies light to selected fibers in a sequential fashion, supplying light for equal non-overlapping periods to each fiber, such that the illumination emanating from the array of optical fibers at the support member 403 progresses in an orbital fashion around central imaging aperture 405. For example, in a presently preferred embodiment, the duration that light is provided to each fiber in the circular array is selectively controlled by the POLS to produce between 2 and 10 "orbits" per second.

Camera 410 provides video images of surface area 406 to video monitor 416 and a video frame store memory 412. A computerized controller arrangement 414, referred to herein as a "frame sequential imaging computer" (FSIPC) controls programmable optical light source 404 and frame store memory 412 so as to capture a video frame image during each sequential illumination of a light source in the borescope probe head. The series of images can then be processed to detect areas having features that change contrast cyclically in a manner indicative of the presence of an anisotropic surface flaw. The FSIPC then highlights or enhances these features on a video image displayed on monitor 415 so as to alert an operator.

In accordance with a further aspect of the present invention, surface image information may be acquired and processed by the FSIPC, as shown in FIG. 4, to form a gray scale intensity (contrast) histogram of each captured and stored image. Such a histogram may be used to isolate and track areas of significant contrast as a function of the direction of illumination. For example, if a flaw were relatively small compared to the surrounding background area, then one would expect to notice a small pixel cluster of intensities (displayed intensity data) "split off" from (outside of) the main intensity distribution. This cluster would cyclically move away from the mean as the defect reflections become brighter. As the orbiting illumination continues to change direction (e.g., for increasing video sequence frames) pass the "peak" reflection brightness, the sub-cluster would then begin moving back toward the mean values and eventually possibly drift below the mean to some minimum value. In evaluating a complete set of histograms, one image may be selected in which a sub-cluster of intensity data (corresponding to a flaw) is maximally separated from the "base" gray scale distribution. The upper and lower gray scale values for such sub-cluster can then be used as upper and lower thresholds to define pixels belonging to a flaw. Pixels within these ranges of brightnesses could then also be color coded and/or displayed as an overlay on top of an original gray scale image so as to alert an operator to potentially important details in an indicated area. In addition, FSIPC 414 is programmed in a conventional manner to calculate and record various physical characteristics of suspected flaws such as area, location, length, width, etc.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An inspection system for imaging and analyzing anisotropically reflecting surface flaws of an object, comprising:
   a camera positioned to acquire a visual image of an area on a surface of an object;
   a disk-shaped annular light source support structure having a light source mounted at an outer periphery, the light source comprising a diverging source of light for illuminating at least a portion of the area, the support structure mounted about a annular roller-bearing and the camera positioned at a center of the annular roller-bearing; and
   a motor-driven friction drive wheel positioned against the support structure so as to cause the support structure to rotate about the camera on the roller-bearing,
   wherein rotation of the support structure causes the light source to progress in an orbital path about an axis extending between a center of image acquiring optics of the camera and a center of the area on the object while illumination from the light source is being directed approximately at the center of the area such that the area is illuminated from a variety of different directions so that any directionally reflective surface flaws will exhibit a detectable change in contrast with respect to immediately surrounding regions.

2. An apparatus for illuminating and imaging directionally reflective flaws existing on the surface of an object, comprising:
   an integral light source and imaging apparatus support structure including a light source and a centrally located imaging apparatus adapted to illuminate and to acquire a visual image of an area on a surface of an object; and
   a remotely located programmable light source controller,
   wherein the light source comprises a plurality of individual sources of illumination positioned around a periphery of the imaging apparatus, each illumination source oriented so as to provide illumination directed substantially toward a center of the area, and each projecting illumination toward said surface from a different predetermined azimuthal angle with respect to said center and a different predetermined elevational angle with respect to the surface;
   said individual sources of illumination being controlled by the light source controller and selectively activated in a predetermined sequence such that the area on the surface of the object is illuminated during discrete intervals from a plurality of different directions without requiring a change in orientation of the object, thereby allowing any directionally reflective surface flaws in an illuminated portion of the area to exhibit a detectable change in contrast with respect to immediately surrounding regions when at least one source of illumination is activated.

3. An apparatus for illuminating and imaging directionally reflective flaws as set forth in claim 2, wherein said individual sources of illumination comprise a plurality of light emitting diodes connected to a programmable remote electrical current source, said current source being programmable so as to selectively activate different light emitting diodes in a predetermined sequence.

4. An apparatus for illuminating and imaging directionally reflective flaws as set forth in claim 2, wherein said individual sources of illumination comprise a plurality of incandescent lamps connected to a programmable remote electrical current source, said current source being programmable so as to selectively activate different lamps in a predetermined sequence.

5. An apparatus for illuminating and imaging directionally reflective flaws as set forth in claim 2, wherein said individual sources of illumination are individually activated, by said programmable light source controller, each for a predetermined period, to provide illumination in a sequential manner in an orbital fashion around a periphery of said imaging apparatus.

6. An apparatus for illuminating and imaging directionally reflective flaws as set forth in claim 2, wherein said imaging apparatus comprises a borescope having an integral miniature video camera electrically connected to a remote frame store memory device for storing video frame information.

7. An apparatus for illuminating and imaging directionally reflective flaws as set forth in claim 2, wherein said individual sources of illumination are arranged in an annulus pattern surrounding said image acquiring portion.

8. An apparatus for illuminating and imaging directionally reflective flaws as set forth in claim 2, wherein said individual sources of illumination are arranged in a plurality of radial arrays surrounding said periphery of the imaging apparatus, each said radial array having at least two sources of illumination.

9. An apparatus for illuminating and imaging directionally reflective flaws as set forth in claim 2, wherein said individual sources of illumination are arranged in a plurality of concentric rings surrounding said imaging apparatus.

10. An apparatus for illuminating and imaging directionally reflective flaws as set forth in claim 2, wherein said individual sources of illumination comprise a plurality of light conducting fibers connected to a remote light source, said light source being controlled by the light source controller so as to selectively provide light to different fibers in a predetermined sequence.

11. An apparatus for illuminating and imaging directionally reflective flaws as set forth in claim 2, wherein said imaging apparatus is a borescope having a fiber optic arrangement for obtaining an image of an area on the surface of said object and providing the image to a remote location.

12. A surface flaw inspection system, comprising:

surface lighting means for illuminating a portion of a surface of an object from a constantly changing direction, said lighting means comprising a plurality of individual sources of illumination arranged to provide light to said surface from a plurality of different directions;

programmable lighting control means for individually activating said individual sources of illumination for a predetermined duration and in a predetermined sequential manner;

imaging means for acquiring a video image of said portion of a surface of an object;

display means for displaying the video image in real time for viewing by a human operator; and image processing means for storing and analyzing a plurality of video frames of said image so as to identify attributes in said image which exhibit intensity fluctuations that are greater than a mean intensity distribution for one or more stored video frames, said processing means including means for displaying said attributes in an enhanced fashion on said display.

13. A method for detecting and analyzing directionally reflective surface flaws on an object, comprising the steps of:

(a) positioning a camera to acquire a visual image of an area on a surface of an object;

(b) illuminating said area using a light source comprised of a plurality of individual sources of illumination positioned around an aperture of the camera, each illumination source oriented so as to provide illumination directed substantially toward a center of the area and projecting from a predetermined azimuthal angle with respect to said center and elevational angle with respect said surface; and (c) sequentially activating individual light sources at separate times, each for a predetermined duration, so that any directionally reflective surface flaws in said portion of the area will exhibit a detectable change in contrast with respect to immediately surrounding regions when at least one source of illumination is activated, (d) acquiring and storing a plurality of images of said surface, each image acquired with the surface illuminated by a different individual light source, and (e) analyzing said images to identify attributes which exhibit intensity fluctuations greater than a predetermined amount from a mean intensity distribution for all images acquired.

* * * * *

UNITED STATES PATENT AND TRADEMARK OFFICE
CERTIFICATE OF CORRECTION

| | |
|---|---|
| PATENT NO. | : 5,774,212 |
| APPLICATION NO. | : 08/821676 |
| DATED | : June 30, 1998 |
| INVENTOR(S) | : Corby, Jr. |

Page 1 of 1

It is certified that error appears in the above-identified patent and that said Letters Patent is hereby corrected as shown below:

In Column 1, immediately below the title, insert:

--The Government of the United States of America has rights in this invention pursuant to Contract No. DE-FC21-95MC31176 awarded by the U. S. Department of Energy.--

Signed and Sealed this

Twentieth Day of February, 2007

JON W. DUDAS
*Director of the United States Patent and Trademark Office*